United States Patent
Riedel

(10) Patent No.: US 11,413,399 B2
(45) Date of Patent: Aug. 16, 2022

(54) INJECTION DEVICE WITH MOUNTING AID FOR A SUPPLEMENTARY DEVICE

(71) Applicant: SANOFI-AVENTIS DEUTSCHLAND GMBH, Frankfurt am Main (DE)

(72) Inventor: Stephan Riedel, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 236 days.

(21) Appl. No.: 15/779,329

(22) PCT Filed: Nov. 25, 2016

(86) PCT No.: PCT/EP2016/078748
§ 371 (c)(1),
(2) Date: May 25, 2018

(87) PCT Pub. No.: WO2017/089502
PCT Pub. Date: Jun. 1, 2017

(65) Prior Publication Data
US 2018/0304028 A1    Oct. 25, 2018

(30) Foreign Application Priority Data
Nov. 27, 2015  (EP) .................................... 15196650

(51) Int. Cl.
*A61M 5/32*    (2006.01)
*A61M 5/24*    (2006.01)
*A61M 5/31*    (2006.01)

(52) U.S. Cl.
CPC ............ *A61M 5/3202* (2013.01); *A61M 5/24* (2013.01); *A61M 5/2459* (2013.01);
(Continued)

(58) Field of Classification Search
CPC .............. A61M 5/3202; A61M 5/2033; A61M 2205/582; A61M 5/3213;
(Continued)

(56) References Cited

U.S. PATENT DOCUMENTS

| 2008/0188813 A1* | 8/2008 | Miller | A61M 5/3202 604/189 |
| 2012/0029442 A1* | 2/2012 | Boyd | A61M 5/3202 604/197 |

(Continued)

FOREIGN PATENT DOCUMENTS

| CN | 1655836 | 8/2005 |
| CN | 103153366 | 6/2013 |

(Continued)

OTHER PUBLICATIONS

International Preliminary Report on Patentability in international Application No. PCT/EP2016/078748, dated May 29, 2018, 7 pages.

(Continued)

*Primary Examiner* — Amber R Stiles
*Assistant Examiner* — Avery Smale
(74) *Attorney, Agent, or Firm* — Fish & Richardson P.C.

(57) ABSTRACT

A mounting aid for attaching a supplementary device to an injection device, wherein the injection device has an elongated housing extending in an axial direction, the mounting aid comprising a body extending in the axial direction, configured to receive at least a portion of the housing and having at least one radially extending engaging member to engage with a correspondingly shaped engaging member of the housing when in a specific position relative to the housing, and wherein the body comprises a side wall with an (Continued)

abutment face facing in a proximal direction, wherein the abutment face is defined on a plane that is inclined to the axial direction.

13 Claims, 7 Drawing Sheets

(52) U.S. Cl.
CPC ............... *A61M 2005/3126* (2013.01); *A61M 2205/3306* (2013.01); *A61M 2205/3375* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/584* (2013.01); *A61M 2205/587* (2013.01)

(58) Field of Classification Search
CPC .. A61M 2005/3215; A61M 2005/3217; A61M 5/2459; A61M 2205/583; A61M 2205/581; A61M 5/1626; A61M 2005/2006; A61M 5/285; A61M 2005/3104; A61M 2005/3109; A61M 2005/3103; A61M 2005/3117; A61M 2005/312; A61M 5/3204; A61M 5/321; A61M 5/3219; A61M 5/50; A61M 39/20; B43K 23/08
See application file for complete search history.

(56) References Cited

U.S. PATENT DOCUMENTS

| | | | |
|---|---|---|---|
| 2012/0053527 A1 | 3/2012 | Cirillo et al. | |
| 2013/0150802 A1* | 6/2013 | Claughton | .......... A61M 5/3202 604/198 |

FOREIGN PATENT DOCUMENTS

| | | |
|---|---|---|
| CN | 104220114 | 12/2014 |
| CN | 104487114 | 4/2015 |
| JP | 2005-522275 | 7/2005 |
| JP | 2008-516711 | 5/2008 |
| JP | 2013-523295 | 6/2013 |
| JP | 2013-530004 | 7/2013 |
| WO | WO 03/086511 | 10/2003 |
| WO | WO 2009/024562 | 2/2009 |
| WO | WO 2011/124634 | 10/2011 |
| WO | WO 2012/001493 | 1/2012 |
| WO | WO 2013/120775 | 8/2013 |
| WO | WO 2014/161955 | 10/2014 |
| WO | WO 2015/136513 | 9/2015 |

OTHER PUBLICATIONS

International Search Report and Written Opinion in International Application No. PCT/EP2016/078748, dated Mar. 1, 2017, 9 pages.

* cited by examiner

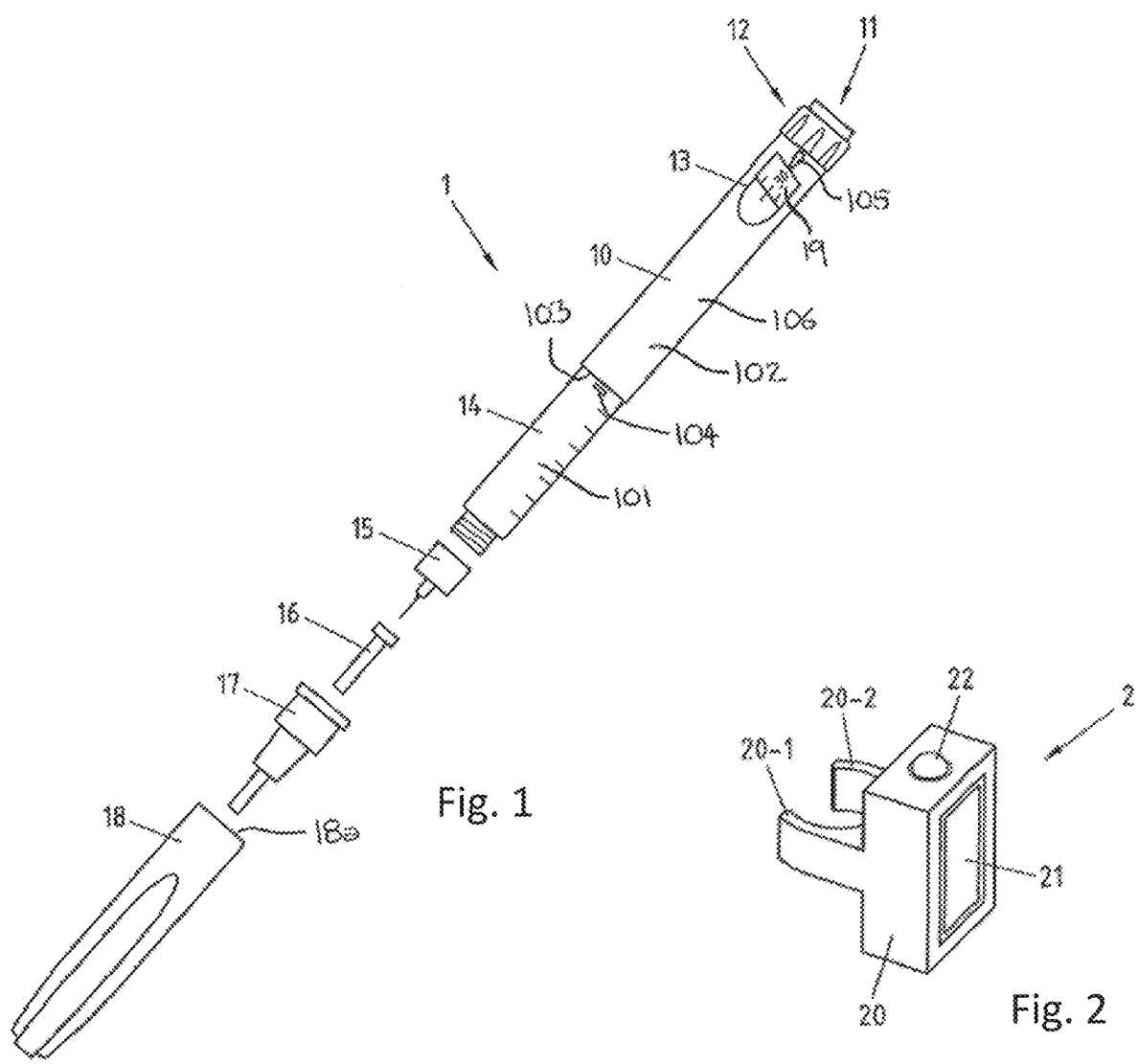
Fig. 1
Fig. 2
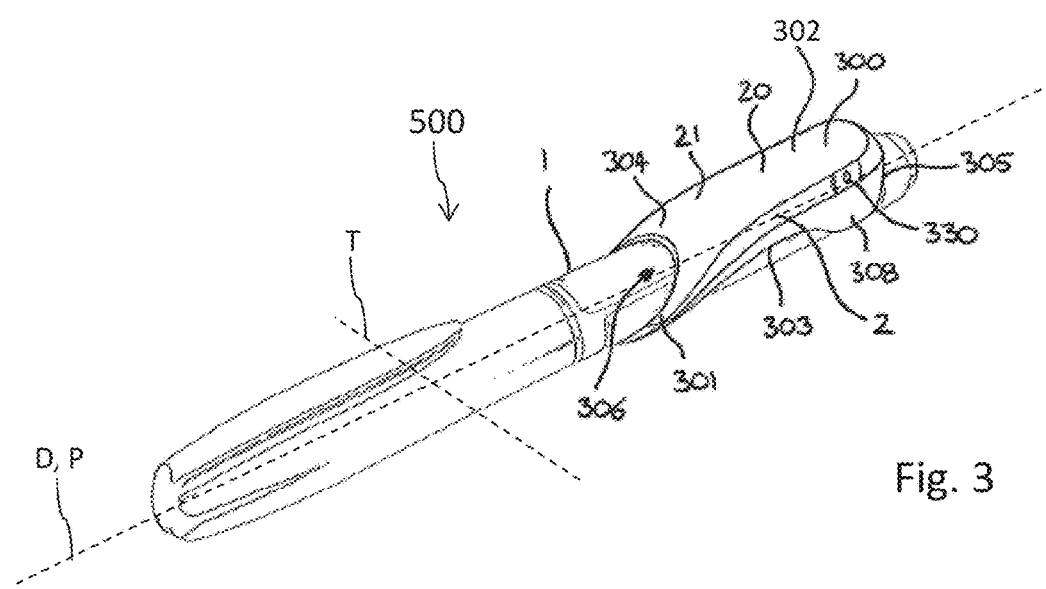
Fig. 3

INJECTION DEVICE WITH MOUNTING AID FOR A SUPPLEMENTARY DEVICE

CROSS REFERENCE TO RELATED APPLICATIONS

This application is a U.S. national stage application under 35 USC § 371 of International Patent Application No. PCT/EP2016/078748, filed Nov. 25, 2016, which claims priority to European Patent Application No. 15196650.4, filed Nov. 27, 2015, the entire contents of each of which are incorporated herein by reference.

TECHNICAL FIELD

The present disclosure generally relates to a supplementary device for an injection device and a mounting aid for attaching a supplementary device to an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. A Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

Furthermore, document WO 2013/120775 A1 describes an electronic clip-on module for a manually operable pen-type injection device. The module configured as a supplementary device has a body and a mating unit configured to releasably mount the body to the injection device in a specific position relative to an outside surface of the injection device for a secure and releasable fastening of the supplementary device to the injection device. A rib protrudes from the outer surface of the injection device that acts as an alignment element for locating a body of the supplementary device in a specific position relative to the outer surface of the injection device.

When properly aligned the rib will be received in a rib-receiving recess in the body of the supplementary device. The supplementary device further comprises protuberances to releasably engage in corresponding indents of the housing of the injection device. When the supplementary device mates correctly with the injection device a haptic feedback from the mating of the protuberances with the indents is provided. But when the supplementary device is not correctly aligned with the injection device in a longitudinal direction or in a circumferential or tangential direction the rib and the rib-receiving recess as well as the protuberances and the indents will not be aligned but will be located offset from each other.

In such a configuration the supplementary device cannot be mounted to the injection device. Moreover, since the mutually mating structures, namely rib-receiving recesses as well as protuberances and indents may not be visible to the user during the progress of mounting the supplementary device to the injection device, a correct alignment and orientation for finally attaching and mounting the supplementary device to the injection device might be somewhat cumbersome and annoying.

SUMMARY

It is desirable to facilitate and to simplify mounting and attachment of a supplementary device to an injection device. In one aspect, the present disclosure describes a mounting aid for attaching the supplementary device to the injection device. Implementation as well as mounting of the mounting aid to the injection device prior to an attachment of the supplementary device to the injection device can be rather simple, cost efficient and intuitive for a user. In another aspect, the mounting aid can fulfill multiple functions. It may replace or substitute a component of an injection device. Said improvements can be implemented into the design and configuration of existing supplementary devices and injection devices. Said improvements can be retrofittable to existing supplementary devices and corresponding injection devices. The present disclosure further describes a kit including an injection device, a mounting aid and a supplementary device. The kit can allow and support a visual and/or haptic control of the attachment procedure when mounting the supplementary device to the injection device.

In one aspect there is provided a mounting aid for attaching a supplementary device to an injection device, in particular to a manually and handheld injection device having an elongated housing that extends in an axial or longitudinal direction. The mounting aid comprises a body also extending in the axial direction when attached to the injection device. The body is configured to receive at least a portion of the housing of the injection device. The body has at least one radially extending engaging member to engage with a correspondingly-shaped engaging member of the housing when in a specific position relative to the housing of the injection device. By means of mutually corresponding engaging members of the body and the housing the body and hence the entire mounting aid can be releasably attached and fixed to the injection device in a single well-defined position and orientation.

The body further comprises a sidewall with an abutment face. The abutment face faces in a proximal direction or is located at a proximally facing end of the body. The abutment face is defined on a plane that is inclined to the axial direction. The abutment face represents a symmetry-breaking feature. It is asymmetric at least with regard to an angular position with regard to a tubular-shaped housing of the injection device. The abutment face is configured to align and to abut with a correspondingly-shaped abutment face of the supplementary device.

The abutment face of the supplementary device also represents a symmetry-breaking feature of the supplementary device so that attaching of the mounting aid to the injection device prior to an attachment of the supplementary device to the injection device provides a mounting support and a well-defined visually as well as haptically detectable geometric structure by the help of which the correct assembly of the supplementary device to the injection device is attainable in a straight forward manner.

Typically, the abutment face of the mounting aid and the abutment face of the supplementary device are correspondingly or complementary-shaped. By preassembling the mounting aid to the injection device in a well-defined and distinct specific position a subsequent mounting and fastening of the supplementary device to the injection device can be facilitated. Fastening and attaching of the supplementary device to the injection device may be conducted with the help of mutually engaging abutment faces of the mounting aid and the supplementary device.

The supplementary device and the injection device may be arrangeable in a preassembly configuration, in which the supplementary device is already in mechanical or physical contact or engagement with the housing of the injection device but in which the supplementary device is at least rotatable or longitudinally translationally displaceable relative to the injection device; and vice versa. In such a preassembly configuration the mounting aid provides support for correctly aligning and correctly orienting the supplementary device relative to the injection device so that mutually corresponding engaging members or engaging structures of the supplementary device and the injection device may engage.

The abutment face of the body of the mounting aid facing in proximal direction serves as a distal stop for the supplementary device, in particular when the supplementary device is attached to the injection device in a distally directed sliding motion relative to the housing of the injection device. Typically, a proximal portion of the injection device is insertable in proximal direction into a receptacle or a collar of the supplementary device. A distally directed displacement of the supplementary device relative to the injection device can be blocked and stopped when the abutment face of the supplementary device, typically facing in distal direction abuts and engages with the correspondingly-shaped proximally facing abutment face of the mounting aid. Since the abutment face of the mounting aid is defined on a plane that is inclined to the axial direction the mounting aid's abutment face not only provides a longitudinal or axial stop but also defines a specific angular position or angular orientation of the supplementary device relative to the injection device.

Correspondingly inclined shapes of the proximal abutment face of the mounting aid and of the distally facing abutment face of the supplementary device only engage and mutually align or completely abut when the supplementary device is correctly oriented with regard to the mounting aid and hence with regard to the injection device. In such a predefined and specific position the supplementary device is easily releasably attachable and fixable to the injection device. When correctly assembled to the injection device the entire distal abutment face of the supplementary device engages or abuts with the entire proximal abutment face of the mounting aid.

According to another aspect the abutment face is planar. The abutment face, i.e. the plane coinciding with the abutment face comprises an imaginary surface normal that extends non-parallel to the axial direction. Typically, the angle between the imaginary surface normal of the abutment face and the axial direction is at least larger than 5°, larger than 10°, larger than 20°, larger than 30° or larger than 45°. Typically, said angle between the imaginary surface normal and the axial direction is smaller than 60°. A planar abutment face is rather easy to manufacture. Moreover, with a planar abutment face the mounting aid can be easily adapted to existing designs of supplementary devices already comprising a complementary-shaped distally facing abutment face or a respective distally facing front face.

The abutment face of the mounting aid does not necessarily have to be planar-shaped. It may comprise concave or convex sections as well as any arbitrary but symmetry-breaking slope or structure by way of which a single well-defined abutment configuration with the supplementary device can be provided. The abutment face of the supplementary device will then typically have a corresponding shape or structure.

In another aspect the body comprises a tubular-shaped receptacle to enclose at least a distal section of the housing. The body of the mounting aid may comprise a cylindrical sleeve to receive at least a major portion or even the entirety of the distal section of the housing of the injection device. Typical injection devices comprise a cartridge holder in a distal housing section. The mounting aid may therefore serve and act as a protective cap for a distal section of the housing or for a cartridge holder of the injection device. The mounting aid may therefore replace or substitute a protective cap of e.g. a pen-type injection device. The mounting aid may provide an at least twofold functionality. It may serve as a mounting aid for the supplementary device and it may further protect the distal section of the injection device.

In another aspect the body is cup-shaped with a closed distal end section. Typically, the body only comprises a single opening at or near its proximal end to receive the distal section of the housing of the injection device. A closed distal end section of the body is particularly configured and designed to prevent ingress of particles or humidity into the interior of the body when attached to the injection device. In typical aspects the abutment face of the body coincides with a proximal end of the body. Hence, the abutment face to engage with a correspondingly-shaped abutment face of the supplementary device is located at a proximal end of the sidewall of the mounting aid's body.

The body may be of tubular shape but may be also provided with a longitudinal slit or recess. Hence, the abutment face may be of annular or oval shape. It may comprise a circumferential closed structure. The abutment face may be also interrupted as seen in tangential or circumferential direction. When assembled to the injection device the abutment face does not necessarily have to enclose the entire circumference of the housing of the injection device. It may be sufficient when only a single or several portions of a proximal end of the mounting aid's body are located in the plane that is inclined to the axial direction. A mutual abutment configuration with the supplementary device will then be obtained via several portions of the proximal end of the body of the mounting aid.

In another aspect the at least one engaging member of the mounting aid protrudes radially inwardly from a sidewall of the body. In this way the at least one engaging member may positively engage with a correspondingly-shaped engaging member on an outside facing portion of the housing of the injection device. By means of the at least one radially extending engaging member the mounting aid is fixable to the injection device with regard to the axial direction and/or with regard to the tangential or circumferential direction. By means of at least one pair of inter-engaging engaging members of the mounting aid and the injection device a well-defined fixing and assembly of the mounting aid to the injection device can be obtained.

According to another aspect the at least one engaging member of the mounting aid comprises an axial stop to axially abut with a correspondingly-shaped axial stop of the housing of the injection device. The axial stop of the housing is typically provided by a correspondingly-shaped engaging member on the outer circumference of the housing. By means of at least one pair of mutually engaging axial stops the mounting aid can be fixed and attached to the injection device at a well-defined and specific axial position. The mutually corresponding engaging members of the mounting aid and of the injection device may provide a positive engagement.

Alternatively, the mutually corresponding engaging members may also frictionally engage. It is even conceivable, that there exist several engaging members or at least two pairs of mutually corresponding engaging members of the mounting aid and of the injection device. Here, at least one pair of mutually corresponding engaging members may positively engage whereas another pair of engaging members may frictionally engage. In another aspect the body comprises at least two oppositely directed or oppositely facing axial stops to simultaneously engage with correspondingly-shaped axial stops of the housing. The axial stops of the housing are also oppositely directed or may face in opposite axial directions, hence in axial proximal direction and in axial distal direction. By having at least two oppositely directed pairs of axial stops on the mounting aid and on the injection device the mounting aid can be fixed to the injection device with regard to both opposite axial directions. In this way the mounting aid can be axially fixed to the injection device.

Oppositely directed axial stops may be provided by means of at least one engaging member of the mounting aid or of the injection device. Hence, one of the body of the mounting aid and the housing of the injection device may comprise a radial recess matching in shape and size with a radial protrusion of the other one of the body and the housing. When the protrusion engages with the correspondingly-shaped recess an axial as well as a tangential mutual engagement of mounting aid and injection device can be obtained.

Alternatively, it is conceivable that the body and the housing comprise numerous axially and/or tangentially separated engaging members to act as a unidirectional axial stop.

In another aspect the at least one engaging member comprises at least one tangential stop to abut in tangential direction with a correspondingly-shaped tangential stop of the housing. Mutually corresponding tangential stops of the body of the engaging member and of the housing of the injection device may at least provide a unidirectional stop feature, e.g. preventing a rotation of the supplementary device relative to the injection device at least in one direction. As already explained above in connection with the axial stops the at least one tangential stop of the mounting aid and the injection device may also provide a bidirectional tangential stop so that at least one pair of engaging members of the mounting aid and of the injection device already provide a fixing and interlocking of the mounting aid to the injection device with regard to the tangential or circumferential direction.

In another aspect the tangential stop is formed by at least one tangential side edge of the engaging member. Here it is particularly conceivable, that the engaging member even provides a twofold tangential stop when having two oppositely located side edges, each of which configured to engage with a correspondingly-shaped tangential stop of the housing of the injection device. As already described above with regard to the axial stops it is also conceivable, that one of the body of the mounting aid and the housing of the injection device comprises a radial protrusion to mate with a correspondingly-shaped and correspondingly-sized recess of the other one of the mounting aid and the injection device.

When the mutually corresponding protrusion and recesses are almost equally sized with regard to the tangential direction their mutual engagement may directly provide a bidirectional tangential or circumferential fixing of the mounting aid to the injection device. In this way the at least one pair of engaging members of the mounting aid and the injection device already provide a rotational interlock between the mounting aid and the injection device.

The mutually corresponding engaging members of the mounting aid and of the injection device may comprise beveled faces and may further comprise flexibly deformable engaging elements in order to provide a positively engaging snap fit connection between the mounting aid and the injection device. There are several alternative ways conceivable to provide a mutual longitudinal and rotational fixing of mounting aid and injection device and the mounting aid is not generally restricted to such positively engaging members.

In another aspect an inner cross-section of a proximal end of the receptacle of the body of the mounting aid is larger than or equal to an outer cross-section of a proximal section of the housing. So when attached to the housing of the injection device the proximal end of the mounting aid is typically located radially outwardly compared to the outer circumference of a proximal section of the housing of the injection device. In this way the mounting aid provides a kind of a radial and circumferential step portion that facilitates a proceeding assembly and attachment of the supplementary device to the proximal portion of the injection device. Here, the abutment face of the mounting aid's body provides a radially outwardly located rim that corresponds and mates with the distally facing abutment face of the supplementary device when attached to the injection device in a predefined specific position.

In a further aspect the body of the mounting aid comprises a visual label on an outside surface. Alternatively, the body comprises a distally extending recess at a proximal end of the sidewall. By means of the visual label or by means of the recess or through opening on or in the sidewall of the mounting aid's body the mounting aid can be correctly assembled in a unique and well-defined way to the injection device. Given that the injection device comprises two geometrically oppositely located engaging members to engage with correspondingly-shaped engaging members of the mounting aid there will be provided two mounting configurations for the mounting aid to the injection device. In this way the mounting aid may be attachable to the injection device in a first configuration and in a second configuration, wherein the second configuration is rotated by 180° with regard to the longitudinal axis compared to the first configuration.

By means of the visual label and/or by means of the recess or through opening on or in the sidewall of the body of the mounting aid the mounting aid can be unambiguously aligned with at least one indicator, e.g. a visual mark or a label that is provided on the outside surface of the injection device. In this way a certain ambiguity of the mechanical interaction between the mounting aid and the injection device can be made unambiguous and unequivocal by means of the visual label or the distally extending recess at the proximal end of the mounting aid's sidewall.

Alternatively it is also conceivable, that mutually engaging and circumferentially distributed engaging members of the mounting aid and the injection device are differently shaped or differently sized so that there are provided different types of engaging members on the mounting aid and on the injection device. So a particular engaging member of the mounting aid may then only engage with a single and complementary-shaped engaging member of the injection device.

In another aspect an injection device is provided that comprises a housing with at least one engaging member to releasably mount a mounting aid as described above in a specific position on an outside surface of the housing. The injection device, in particular its housing further comprises at least one engaging structure to releasably mount a supplementary device in a specific position on the outside surface of the housing. The injection device further comprises a mounting aid as described above which is attached or which is attachable to the housing of the injection device.

The mutually corresponding engaging members of the injection device and of the mounting aid are configured such, that the mounting aid is attachable and fixable to the injection device in a single and unambiguous specific position, in which the abutment face of the mounting aid provides a well-defined geometric structure relative to the injection device. The abutment face of the mounting aid corresponds with a complementary-shaped abutment face of the supplementary device. The abutment face of the supplementary device is configured and aligned with regard to at least one engaging member of the mounting aid in such a way that when the mutually corresponding abutment faces of the mounting aid and the supplementary device abut the at least one engaging member of the supplementary device is correctly aligned and oriented with regard to the engaging structure of the injection device. In this configuration a mutual assembly and fastening of the supplementary device to the injection device is rather intuitive and straight forward.

In another aspect the housing comprises a distal section and a proximal section. The at least one engaging member of the housing of the injection device is located on the outside of a sidewall of the distal section and comprises a longitudinal recess to positively engage with the at least one radially extending engaging member of the mounting aid. The longitudinal recess may be configured as a recessed portion having a radial depth that is smaller than the thickness of the sidewall of the distal section. Alternatively, the longitudinal recess comprises a through opening and resembles a longitudinal slit that is adapted and configured to receive the radially inwardly protruding engaging member of the mounting aid when assembled to the injection device.

The distal section of the housing is typically configured as a cartridge holder and the proximal section of the housing may be commonly denoted as a body of the housing. The cartridge holder is typically configured to accommodate and to enclose a container filled with a medicament. Typical containers comprise a cartridge having a vitreous barrel sealed in distal direction by means of a pierceable seal and having a proximal seal in form of a plunger of piston being displaceable in distal direction so as to expel a predefined amount of the medicament through the distal seal when punctured by a double tipped injection needle. The body of the housing typically accommodates a drive mechanism having at least a longitudinally or axially extending piston rod that is displaceable in distal direction so as to apply a distally directed thrust to the piston of the cartridge.

The drive mechanism may further include numerous inter-engaging mechanical components, such like a drive sleeve, at least one clutch element and a dose display member by way of which the size of a dose actually set can be visually displayed in a window of the housing. The supplementary device is particularly configured to record a sequence of doses that are dispensed by the injection device. For this the supplementary device may comprise some kind of image acquisition and number recognition means in order to detect and to store consecutive doses dispensed by means of the injection device.

According to another aspect the injection device comprises a visual label at a specific circumferential section on the outside surface of the housing. The visual label may provide medicament related information. The visual label is attached to a well-defined portion of the housing. By means of the visual label or by means of some other kind of visual indicator or mark a potentially ambiguous mechanical attachment of the mounting aid to the injection device can be set aside. By means of the visual label on the outside surface of the housing coinciding with or completing a visual label at a proximal end of the sidewall of the mounting aid, the mounting aid can be attached and fixed to the injection device in an unambiguous and well-defined way.

The injection device may be configured as a disposable or as a reusable injection device. When configured as a disposable injection device the device is equipped with a cartridge filled with the respective medicament. With a disposable device the entire device is intended to be discarded after the content of the cartridge has been used up. With disposable devices a distal housing section and a proximal housing section of the injection device are permanently and non-detachably connected. When implemented as a reusable injection device the distal housing part and the proximal housing part may be of detachable and re-connectable type so as to enable replacement of an empty cartridge and to support a reset operation of the drive mechanism.

In still another aspect a kit is provided that comprises an injection device as described above and that further comprises a supplementary device having a body and at least one engaging member to releasably mount the body in a specific position on the outside surface of the injection device. The body of the supplementary device comprises an abutment face to align and to abut with the above mentioned abutment face of the mounting aid, which is typically pre-assembled to the injection device. The distally facing abutment face of the supplementary device typically aligns and abuts with the proximally facing abutment face of the mounting aid when attaching the supplementary device to the injection device.

The term "distal direction" or "distal end" denotes a direction or end of a device that points towards an injection site of a patient. The "proximal direction" or "proximal end" denotes a direction or end of a device that points away from an injection site of a patient. Distal and proximal directions coincide with the longitudinal axis of the injection device but point in opposite directions.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, embodiments of the injection device and the supplemental device are described in detail by making reference to the drawings, in which:

FIG. 1 schematically shows a manually operable injection device,

FIG. 2 shows a schematic illustration of a supplementary device to be releasably attached to the injection device of FIG. 1, FIG. 3 shows a perspective view of the supplementary device of FIG. 2 releasably attached to the injection device of FIG. 1.

DETAILED DESCRIPTION

Figure 4:
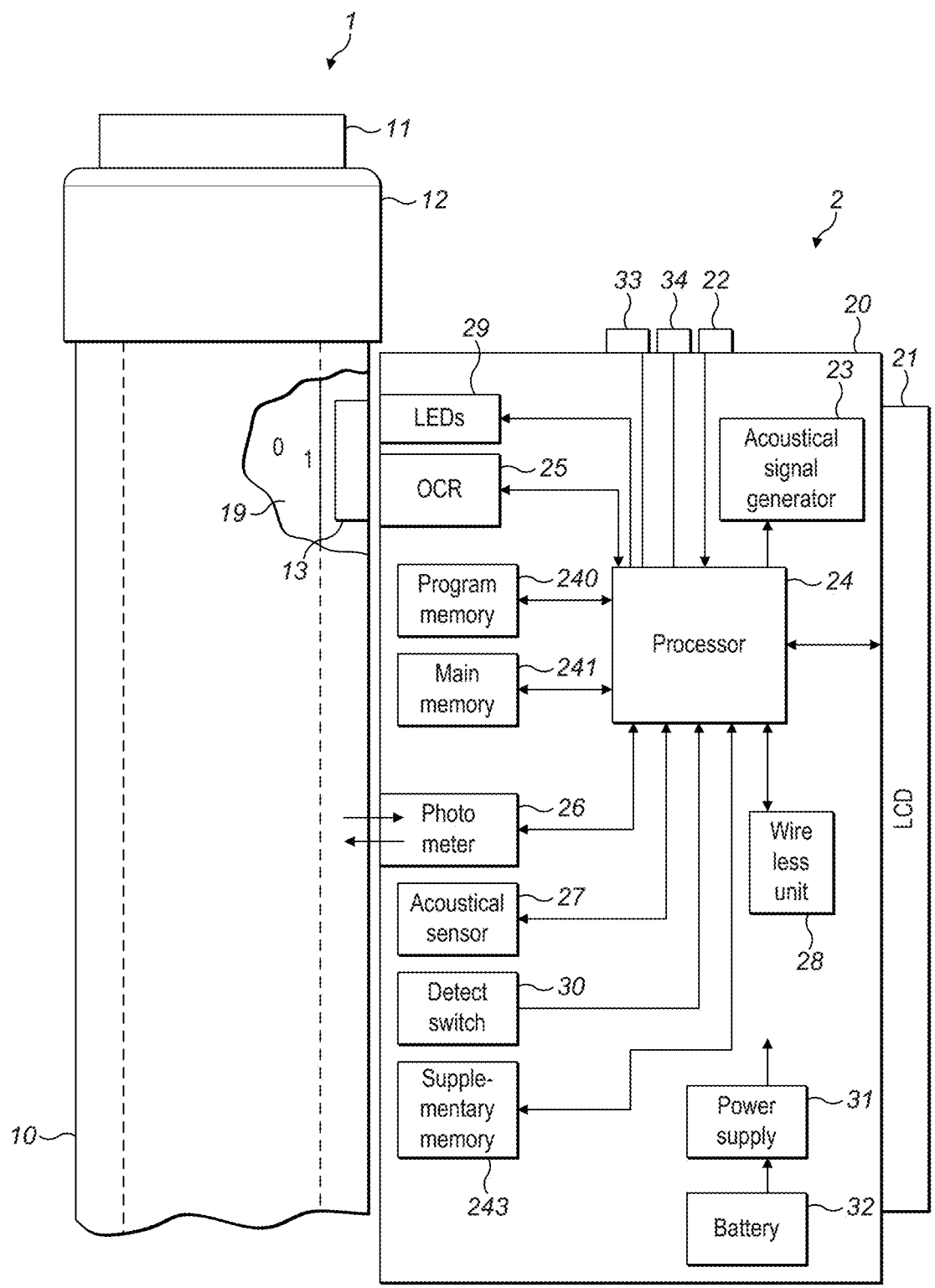
FIG. 4 shows a schematic view of the supplementary device in a state where it is mounted to the injection device.

FIG. 1 is an exploded view of an injection device 1, which may for instance represent Sanofi's Solostar® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning a dosage knob 12, and the selected dose is then displayed via a dosage window or display 13, for instance in multiples of so-called International Units (IU), wherein one IU is the biological equivalent of about 45.5 micrograms of pure crystalline insulin (1/22 mg). An example of a selected dose displayed in dosage window or display 13 may for instance be 30 IUs, as shown in FIG. 1. It should be noted that the selected dose may equally well be displayed differently, for instance by an electronic display. It will be understood that dosage window relates to the section of the injection device through or on which the selected dosage is visible.

Turning the dosage knob 12 causes a mechanical click sound to provide acoustical feedback to a user. The numbers displayed in dosage window or display 13 are printed on a sleeve 19 that is contained in housing 10 and mechanically interacts with a piston in the insulin container 14. When needle 15 is stuck into a skin portion of a patient, and then injection button 11 is pushed, the insulin dose displayed in display 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached. Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards. For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

The housing 10 of the injection device 1 comprises a front section 101 and a rear section 102. The needle 15 is affixed to the front end of the front section 101 and the dosage knob 12 extends from the rear end of the rear section 102. The front section 101 has a smaller diameter than the rear section 102 of the injection device housing 10.

A shoulder 103 is defined between the front section 101 and the rear section 102. The shoulder 103 extends circumferentially around the housing 10. The cap 18 extends over the front section 101. The cap 18 covers the front section 101 and a lip 18a of the cap 18 locates against the shoulder 103.

A cap retaining ridge 104 is formed on the outer surface of the front section 101 of the housing 10 of the injection device 1. The cap retaining ridge 104 is disposed proximate to, but spaced from, the shoulder 103. The ridge 104 extends diametrically about the front section 101. The ridge 104 locates over one or more retaining elements (not shown) formed on the inner surface of the cap 18 to retain the cap 18 in position over the front section 101. Alternatively, the cap retaining ridge 104 locates in a corresponding diametrically extending recess (not shown) formed on the inner surface of the cap 18.

The injection device 1 further comprises additional elements. A rib 105 protrudes from an outer surface 106 of the injection device 1. The rib 105 acts as an alignment element for locating the body in a specific position relative to the outer surface 106 of the injection device 1. The rib 105 upstands from the outer surface 106 of the injection device 1 between the dosage display 13 and the dosage knob 12. The dosage knob 12 is disposed on the rear section 102 of the injection device housing 10. The rib 105 is elongate and extends parallel to the longitudinal axis of the injection device 1.

Left and right engaging structure 107 actually formed as indents 107 (refer to FIG. 6) are formed in the outer surface 106 of the injection device 1. The two indents 107 are formed in the rear section 102. Each indent 107 is formed proximate to the rear end of the injection device housing 10. The indents 107 are formed generally diametrically opposite to each other on left and right sides of the injection device 1. The indents 107 have chamfered sides.

Figure 8:
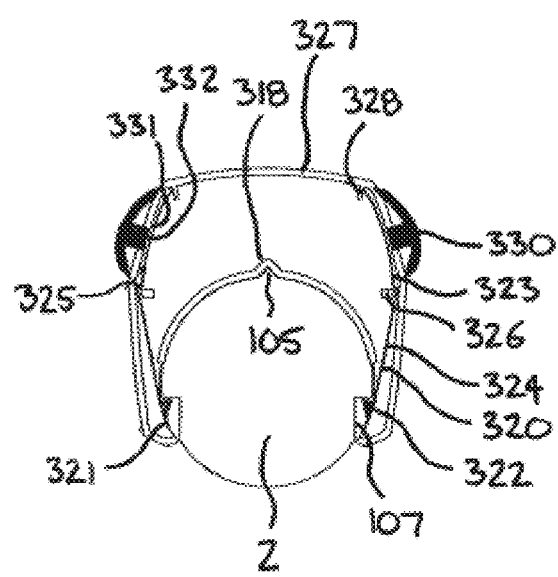
FIG. 8 shows a cross-sectional rear view of the supplementary device releasably attached to the injection device with resilient arms of a fixing unit in an engaged position with the injection device.

FIG. 2 is a schematic illustration of an embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1, for instance when the injection device 1 is empty and has to be replaced. FIG. 2 is highly schematic, and details of one embodiment of the physical arrangement are described below with reference to FIG. 3. The wings or clip features 20-1 and 20-2 as shown in FIG. 2 generally represent engaging members 140 by way of which the supplementary device 2 is releasably attachable to the outer surface of the injection device 2. The engaging members 140 as shown in FIG. 8 may be generally realized in many different ways, e.g. by mutually engaging positive interlock means, such like resilient clip members.

Supplementary device 2 contains optical and acoustical sensors for gathering information from injection device 1. At least a part of this information, for instance a selected dose (and optionally a unit of this dose), is displayed via display unit 21 of supplementary device 2. The dosage display 13 of injection device 1 is obstructed by supplementary device 2 when attached to injection device 1.

Supplementary device 2 further comprises three user input transducers, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

FIG. 3 shows a view of the supplementary device 2 with the arrangement of the mating unit and housing shown in greater detail. The supplementary device 2 is shown mounted to the injection device 1 in FIG. 3. The housing 20 of the supplementary device 2 has a body 300 and a collar 301. The body 300 is elongate and the display unit 21 is disposed on an upper side 302 of the body 300. The collar 301 extends from a lower side 303 of the body 300. The body 300 has a front end 304 and a rear end 305. The collar 301 extends from the front end 304. The collar 301 extends from the body 300 at an acute angle to the longitudinal axis of the elongate body 300.

The collar 301 has an aperture 306 formed therethrough. The collar 301 is configured to receive the injection device 1 through the aperture 306. A channel 307 (refer to FIG. 6) is formed in the lower side 303 of the body 300. The channel 307 is elongate and extends between the front end 304 and the rear end 305 of the body 300.

Two wings 308, acting as protective walls, extend downwardly from the lower side 303 of the body 300. The wings 308 are spaced from each other and distend from either side of the channel 307. Therefore, the injection device 1 is receivable between the wings 308. The wings 308 are disposed at the rear end 305 of the body 300, at an opposite end of the body 300 to the collar 301.

The collar 301 and channel 307 form part of an alignment arrangement or alignment unit. The alignment unit is configured to locate the body in a specific position relative to the outside surface 106 of the injection device 1. The alignment unit forms part of the mating unit configured to embrace the housing 10 of injection device 1 to maintain the supplementary device in a specific position on the injection device 1.

The supplementary device 2 further comprises an engaging unit or arrangement configured to releasably mount the body to the injection device 1. The collar 301 also forms part of the engaging unit. The engagement unit forms part of the mating unit.

The features that contribute to correct alignment of the supplementary device 2 on the injection device 1 can be termed an alignment arrangement or alignment unit. The features that contribute to engagement of the supplementary device 2 to the injection device 1 can be termed an engaging unit or engaging arrangement.

FIG. 4 shows a schematic view of the supplementary device 2 of FIG. 2a in a state where it is attached to injection device 1 of FIG. 1. With the housing 20 of supplementary device 2, a plurality of components are comprised. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

A supplementary memory 243 may also be used to store a logbook on performed ejections/injections. Program memory 240 may for instance be a Read-Only Memory (ROM), main memory 241 may for instance be a Random Access Memory (RAM), and supplementary memory 243 may for instance be a flash memory. The supplementary memory 243 may comprise part of the supplemental device 2 or may alternatively be removably couplable thereto by a USB-type interface for instance or other connection.

In an example embodiment, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. The buttons 22, 33, 34 may be any suitable form of user input transducers, for instance mechanical switches, capacitive sensors or other touch sensors.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage display 13, in which a currently selected dose is displayed (by way of numbers printed on the sleeve 19 contained in injection device 1, which numbers are visible through the dosage display 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage display 13, in which a currently selected dose is displayed. A diffuser may be used in front of the light-sources, for instance a diffuser made from a piece of acrylic glass. Furthermore, the optical sensor may comprise a lens (e.g. an aspheric lens) leading to a magnification (e.g. a magnification of more than 3:1)

Processor 24 further controls a photometer 26, that is configured to determine an optical property of the housing 10 of injection device 1, for example a color or a shading. The optical property may only be present in a specific portion of housing 10, for example a color or color coding of sleeve 19 or of an insulin container comprised within injection device 1, which color or color coding may for instance be visible through an opening or window in housing 10 (and/or in sleeve 19). Information on this color is then provided to processor 24, which may then determine the type of injection device 1 or the type of insulin contained in injection device 1 (e.g. SoloStar Lantus with purple color and SoloStar Apidra with blue color). Alternatively, a camera unit may be used instead of photometer 26, and an image of the housing, sleeve or insulin container may then be provided to processor 24 to determine the color of the housing, sleeve or insulin container by way of image processing. Further, one or more light sources may be provided to improve reading of photometer 26. The light source may provide light of a certain wavelength or spectrum to improve color detection by photometer 26. The light source may be arranged in such a way that unwanted reflections, for example by dosage display 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1. A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

The mating unit and mutually interacting engaging members of the injection device 1 and the supplementary device 2, such like for releasably mounting the supplementary device to the injection device in a specific position relative to an outside surface of the injection device will now be described in detail.

The correct alignment of the supplementary device 2 on the injection device 1 ensures that the OCR reader 25 is correctly aligned with the dosage window 13. Correct alignment allows correct operation and reliable readings. Ensuring that there can be correct alignment between the supplementary device 2 and the injection device 1 in use allows a simpler design for the OCR reader 25, in particular because it does not need to be designed to be able to accommodate different alignments between the devices 1, 2.

Figure 5:
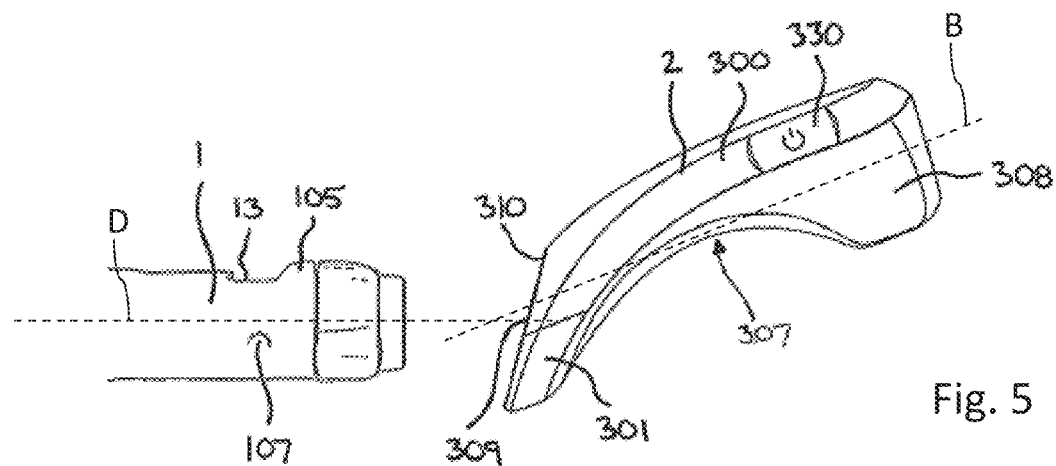
FIG. 5 shows a perspective side view of the supplementary device oriented to be mounted to the injection device.

Referring to FIG. 5, the supplementary device 2 is shown prior to mounting the supplementary device 2 on the injection device 1. In FIG. 5, the supplementary device 2 is shown orientated relative to the rear section 102 of the housing 10 of the injection device 1 so that the rear section 102 is receivable through the aperture 306 formed in the collar 301.

The housing 20 of the supplementary device 2 comprises the body 300 and the collar 301. The elongate body 300 has a longitudinal axis, with the collar 301 distending downwardly from the front end 304 of the body 300. The channel 307 (refer to FIGS. 7 and 8) formed in the lower side 303 of the body 300 extends from the aperture 306 formed in the collar 301. Therefore, an upper portion of the aperture 306 forms part of the elongate channel extending between the front end and the rear end of the housing 20.

The aperture 306 has a front opening 309. The front opening 309 is formed in a front face 310 of the housing 20. The front face 310 may be planar. The edge of the front opening 309 is defined on a plane extending at an angle to the longitudinal axis of the elongate body 300. The front opening 309 has an elliptical shape. The width of the front opening 309 at its minor axis or conjugate diameter corresponds to or is slightly greater than the diameter of the rear section 102 of the injection device 1. The width of the front opening 309 at its major axis or transverse diameter is greater than the diameter of the rear section 102 of the injection device 1. It will be understood that the rear section 102 of the injection device 1 is receivable through the opening 309 so that it extends through the aperture 306.

Figure 7:
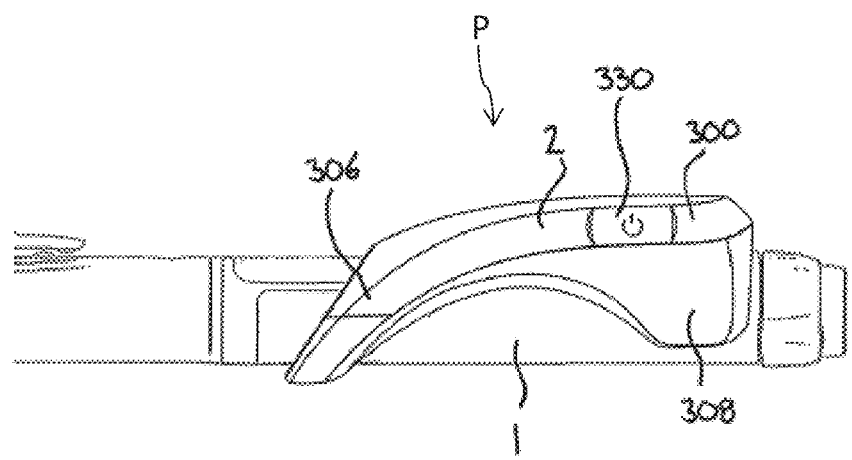
FIG. 7 shows a side view of the supplementary device releasably attached to the injection device.
Figure 9:
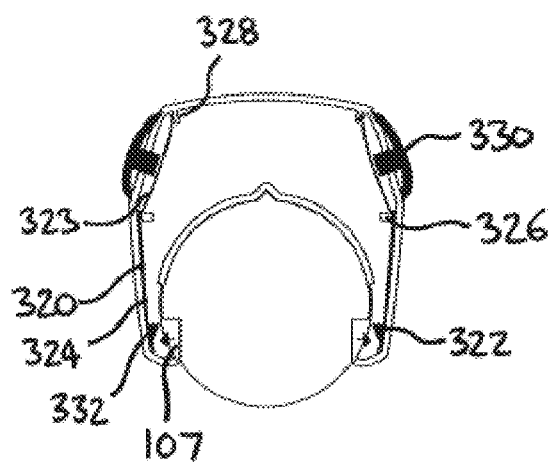
FIG. 9 shows a cross-sectional rear view of the supplementary device releasably attached to the injection device with resilient arms of a fixing unit in a disengaged position with the injection device, FIG. 10 schematically shows the mounting aid and the injection device prior to a mutual assembly.
Figure 10:
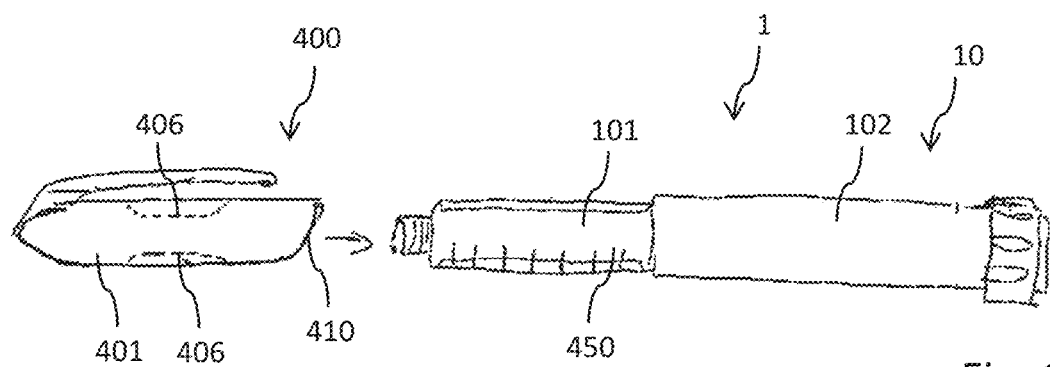

The channel 307 is shown in FIGS. 7 to 9. The channel 307 has a base 312. The base 312 of the channel 307 is arcuate in cross-section. The base 312 extends parallel to the longitudinal axis of the body 300. The shape of the base 312 corresponds to the outer surface of the rear section 102 of the injection device 1. Therefore, the rear section 102 of the injection device is receivable therein and the outer surface of the injection device 1 locates against the channel base 312. The optical sensor 25 is embedded in the channel base 312 to face into the channel 312.

The collar 301 defines an upper part 314 and a lower part 315. The upper part 314 is integrally formed with the body 300 and thus extends from the base 312 of the channel 307. The lower part 315 opposes, but is at least partially offset from, the upper part 314. In the present embodiment, the upper part 314 is defined by the upper half of the inner surface of the collar 301 and the lower part 315 is defined by the lower half of the inner surface of the collar 301. The inner surface of the collar 301 defines a cylinder, with the base 312 of the channel 307 extending from the cylindrical surface. Therefore, the arcuate base of the channel 307 and the inner cylindrical surface of the collar are formed to arc about the same longitudinal axis.

A lower locating surface 317 is defined on the lower part 315 of the collar 301. An upper locating surface 316 is defined on the upper part 314 of the collar 301. The upper and lower locating surfaces oppose each other. When the injection device is received through the aperture, the upper and lower locating surfaces 316, 317 are configured to locate against the outer surface of the injection device 1. the locating surfaces 316, 317 are brought into contact with the injection device 1 by rotating the supplementary device 2 about an axis extending perpendicular to the major axis of the opening 309 so that the upper and lower locating surfaces are moved towards the outer surface of the injection device 1. The central axis of the cylindrical aperture extending through the collar is brought into co-axial alignment with the longitudinal axis of the injection device 1.

In the present embodiment, the base 312 of the channel extends co-planar with the upper part of the collar 301. Therefore, the base 312 of the channel also locates against the outer surface of the injection device 1 when the supplementary device 2 is rotated about an axis extending perpendicular to the major axis of the opening 309 so that the upper and lower locating surfaces are moved to lie against the outer surface of the injection device 1. Therefore, it will be understood that the upper locating surface may be formed by the upper part 314 of the collar, or by the base 312 of the channel 307. Alternatively, the lower locating surface is formed on one or more locating elements protruding into the aperture from the lower part of the collar. Similarly, the upper locating surface is formed on one or more locating elements protruding into the aperture or the injection device receiving channel.

A rib receiving recess 318 (refer to FIGS. 8 and 9) is formed in the base 312 of the channel 307. The rib receiving recess 318 is dimensioned to receive the rib 105 protruding from the outer surface 106 of the injection device 1. The rib receiving recess 318 is dimensioned so as to correspond closely to the shape and size of the locating rib 105 that is present on the injection pen 1. The rib receiving recess 318 is slightly larger than the locating rib 105 so as to ensure that the locating rib 105 can be easily located within the recess. Therefore, the rib 105 acts as an alignment element for locating the body in a specific position P relative to the outer surface 106 of the injection device 1 when the rib 105 is received in the rib receiving recess 318. The rib receiving recess 318 therefore aids the correct alignment and orientation of the body 300 on the injection device 1.

The rib receiving recess 318 is formed at the end of the supplementary device 2 that is closest to the dosage knob 12 when the supplementary device 2 is fitted to the injection device 1. Left and right arms 320, acting as support members, extend below the injection device receiving channel 307 on left and right sides of the body 300. As shown in FIGS. 8 and 9, a lower part 324 of each arm 320 depends substantially vertically from the lower side of the body 300 of the supplementary device 2. Therefore, the arms 320 extend either side of the injection device receiving channel 307 and are spaced from each other.

The left arm 320 has a left protuberance 322 disposed at a free end 321 of the lower part 324. The right arm 320 also has a right protuberance 322 disposed at a free end 321 of the lower part 324. Each protuberance 322 acts as an engaging element to engage in the indents 107 formed in the outer surface of the rear section 102 of the injection device 1. The protuberance 322 on the left arm 320 is configured to be received in the left indent 107. The protuberance 322 on the right arm 320 is configured to be received in the left indent 107. The protuberances 322 are shaped to correspond to the shapes of the indents 107 respectively. In this way, the protuberances 322 fit within the corresponding indents 107 respectively when the supplementary device 2 is correctly positioned on the injection device 1. The external dimensions of the protuberances 322 are slightly smaller than the internal dimensions of the indents 107 so as to ensure that the protuberances 322 fit within their respective indent.

In the present embodiments, the right protuberance 322 is shaped to correspond closely to the shape of the right indent 107. In this way, the right protuberance 322 fits snugly within the right indent 107 when the supplementary device 2 is correctly positioned on the injection pen 1. The left protuberance 322 is shaped similarly to the right protuberance 322, although it is less tall. Put another way, it is like the right protuberance 322 but with the top part is missing or cut off. This is the reason for the end face of the left protuberance 322 having a larger area than the right protuberance 322. The different sizes for the protuberances 322 helps the protuberances find engagement within the indents 107. The right protuberance 322 can be considered to be a master to the left protuberance 322, which is a slave.

Each arm 320 has an upper part 323 and a lower part 324. A step 325 is formed at a mid section of each arm 320, with the upper part 323 depending from one side of the step 325 and the lower part 324 depending from the other side. The protuberance 322 is formed at the free end of the lower part 324. The lower part 324 extends from the step 325 at an angle to the upper part 323.

A support element 326 is disposed in the left side of the body 300. Another support element 326 is disposed in the right side of the body 300. Each support element 326 is disposed in the body 300 and spaced from an outer shell 327 of the body 300 to define a gap. The left arm 320 is received in a left side of the body 300. The right arm 320 is received in a right side of the body 300. The arms 320 are disposed behind the wings 308 that depend from the body 300. The wings 308 may be formed from a transparent material. This allows a user to be able to view the locations of the arms 320 relative to the indents 107, which may help the user to locate the supplementary device 2 correctly on the injection device 1.

As can be seen from FIG. 8, the wings, or protective walls 308, extend slightly further in a downwards direction than the arms. The left arm 320 extends through the gap formed in the left side of the body 300 and the right arm 320 extends through the gap on the right side of the body 300. The step 325 formed at the mid-section of each arm 320 locates against the corresponding support element 326. The step 325 locates each arm 320 so that the lower part 324 extends below the support element 326. The end of the upper part 323 of each arm 320 locates against a tab 328 extending from an inner surface of the body outer shell 327. The upper part 323 of each arm 320 is therefore retained in position in the body 300 and extends between the support element 326 and the tab 328.

The distance between each support element 326 and tab 328 is slightly less than the length of the upper part 323 of each arm 320. Therefore, when the upper part 323 of each arm 320 is disposed between the corresponding element 326 and the tab 328, the upper part 323 of each arm 320 is deformed to have an arcuate shape. Each arm 320 is resilient. The upper part 323 bows into a convex shape towards the outer shell of the body 300. Therefore, the step 325 is biased against the support element 326 and the free end of the upper part 323 is biased against the tab 328. The upper part 323 of each arm 320 between the free end and the step is urged towards the outer shell 327.

The lower part 324 of each arm 320 extends from the upper part 323 and through the gap defined between the support element 326 and the outer shell 327. The lower parts 324 of the arms 320 are splayed towards each other, extending from the support element 326. The effect of the resilience of the upper part 323 of each arm 320 is to bias the lower part 324 of each arm 320 into a certain position. The position into which the lower part 324 of each arm 320 is initially located is such that the distance between the innermost surfaces of the protuberances 322 is slightly less than the distance between the bottoms of the indents 107. The effect of the bias of each arm 320 is to resist movement of the protuberances 322 and the lower parts 324 of the arms 320 away from one another.

The arms 320, acting as support members, are restrained from moving in a direction along the longitudinal axis of the elongate body 300. This assists in maintaining the supplementary device 2 in the correct location after engagement of the supplementary device on the injection pen 1 even in the presence of forces acting to move the supplementary device 2 along the longitudinal axis of the injection pen 1. The arms 320 can be termed support members because they support the protuberances.

Left and right buttons 330 are mounted on the left and right sides of the body 300. An aperture 331 is formed through the outer shell 327 on each side of the body 300. A protrusion, acting as an actuating element 332, is formed on the rear side of each button 330 and extends through the corresponding aperture 331 to act on the upper part 323 of the corresponding arm 320 and apply a biasing force thereon.

When one of the buttons 330 is pressed inwardly by a user the actuating element 332 of each button 330 is biased inwardly. The actuating element 332 urges against the convex surface of the upper part 323 of the corresponding arm 320. The upper part 323 then deforms under the force applied by the actuating element 332. The support element 324 acts as a fulcrum and the arm 320 is urged to pivot about the support element. The distal end of the upper part 323 is prevented from moving by the tab 328 against which the upper part 323 is located. However, the free end 321 of the lower part 324 is free to move outwardly and so the lower part 324 pivots about the support element 324.

When both buttons 330 are pressed, the lower parts 324 of the two arms 320 are urged to rotate about their respective support elements 324. Therefore, the free ends 321 of the arm lower parts 324 are urged away from each other. The release of the pressing force on each button releases the biasing force acting on the upper part 323 of each arm and so the lower part of each arm is urged to return to its neutral position due to the resilience of the arms 320.

As is shown in FIG. 5, the supplementary device 2 is initially located with respect to the injection pen 1 such that the opening 309 to the aperture 306 in the collar 301 is aligned with the rear end of the injection device 1. The body 300 is orientated so that the longitudinal axis B of the injection device receiving channel 307 is inclined with respect to the longitudinal axis D of the injection device 1.

Figure 6:
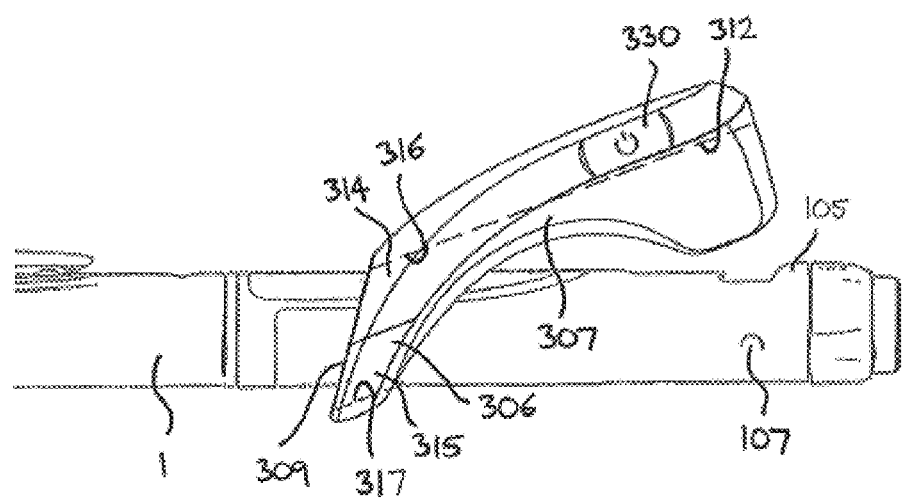
FIG. 6 shows a side view of the supplementary device with the injection device received through a collar of the supplementary device.

The collar 301 is then slid over the rear section 102 of the injection device 1, as shown in FIG. 6. The width of the front opening 309 at its minor axis or conjugate diameter corresponds to or is slightly greater than the diameter of the rear section 102 of the injection device 1. The width of the front opening 309 at its major axis or transverse diameter is greater than the diameter of the rear section 102 of the injection device 1. Therefore, the rear section 102 of the injection device 1 is received through the aperture 306 of the collar 301.

In order to locate the supplementary device 2 on the injection device 1, the supplementary device 2 is rotated relative to the injection device 1 about the transverse axis T extending perpendicular to the major axis of the opening 309, hence the longitudinal axis B of the supplementary device 2. The longitudinal axes D of the injection device 1 and the injection device receiving channel 307 are rotated towards each other. Furthermore, the upper and lower locating surfaces 316, 317 are moved towards the outer surface of the injection device 1.

As the supplementary device 2 and injection device 1 are rotated relative to each other the free ends 321 of the right and left arms 320, in particular the protuberances 322, brought into contact with the outer surface of the injection device housing 10. The protuberances 322 here contact the housing to the left and right sides of the display window 13.

In order to engage the supplementary device 2 with the injection device 1, the user first arranges the supplementary device 2 with respect to the injection device 1 as shown in FIG. 6, and then applies a further force downwards on the supplementary device 2 while at the same time applying a force upwards on the injection device 1. Therefore, the supplementary device 2 and injection device are urged to rotate relative to each other about the collar 301. A biasing force is therefore applied to the protuberances 322 by the outer surface of the rear section 102. As the injection device 1 and the supplementary device 2 are urged to move closer together, the biasing force results in the arms being urged away from each other.

The lower part 324 of each arm 322 is urged to deflect outwardly, and to pivot about the corresponding support element 326. However, the upper part 323 of each arm is prevented from pivoting by the corresponding tab. This causes a reaction force to be applied by the lower part 324 of each arm due to the resilience of each arm 320, which resists entry of the injection device 1 into the injection device receiving channel 307. However, as the supplementary device 2 is further rotated over the injection device 1, the protuberances 322 become aligned with the left and right indent 107 and, due to the resilience of the arms 320, engage with the indents 107.

Referring to FIG. 7, as the supplementary device 2 is further rotated with regard to the transverse axis T to engage the protuberances 322 in the indents 107, the rear section of the injection device 1 is received in the injection device receiving channel 207. The lower locating surface 317 of the collar 301 is urged into contact with a lower side of the outer surface of the injection device 1 and the upper locating surface 316 is urged into contact with an opposing side of the outer surface of the injection device 1. Once the protuberances 322 engage in the indents 107, there is significant resistance to further movement of the supplementary device 2 relative to the injection device 1, due in part to the lower and upper locating surfaces 316, 317 abutting the outer surface of the injection device. The upper and lower locating surfaces 316, 317 are partially offset from each other, with the upper locating surface 317 being disposed between the lower locating surface and the protuberances 322. Movement of the supplementary device 2 relative to the injection device 1 in the opposite direction is restricted by the protuberances 322 being engaged in the indents 107. The injection device 1 also locates against the base 312 of the channel 307.

It will be understood that the body 300 is mated to the injection device 1 by the collar 301 extending circumferentially around the injection device 1 at a front end of the body 300, and the protuberances 322 engaging in the indents 107 at the rear end of the body 300.

In FIGS. 10-15 one embodiment of a mounting aid 400 for attaching the supplementary device 2 to the injection device 1 is illustrated. The mounting aid 400 is configured as a protective cap 18. It is provided with special technical features by way of which it effectively serves to support and to facilitate attachment of the supplementary device 2 to the injection device 1. The mounting aid 400 comprises a body 401, which when attached to the injection device 1 also extends in axial direction, hence along the long axis D of the injection device 1. Throughout the Figures an axial distal direction is denoted with reference number 3 whereas an opposite and proximal axial direction is denoted with reference number 4. The body 401 of the mounting aid comprises a somewhat tubular-shaped sidewall 402 that forms a cup-shaped receptacle 403 to receive a distal or section 101 or front section of the housing 10 of the injection device 1. The mounting aid 400 is also equipped with a clip 405 in order to fasten the entire injection device 1 e.g. to a pocket.

Figure 11:
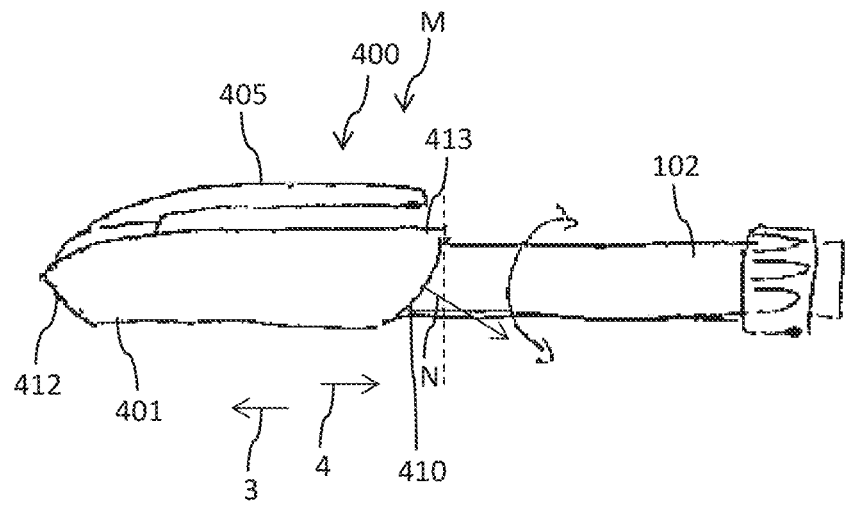
FIG. 11 shows the mounting aid attached to the injection device in a specific position.

The distal end 412 of the body 401 is typically closed so as to confine the interior volume of the receptacle 403 in distal direction 3. Near its proximal end 413 the mounting aid 400 comprises an opening to receive the distal section 101 of the injection device 1. Near or at the proximal end 413 the body 401 further comprises an abutment face 410 that faces substantially in proximal direction 4. The abutment face 410 is defined on a plane that is inclined to the axial direction and hence to the axial elongation of the tubular-shaped body 401. The inclination is expressed by the imaginary surface normal N as shown in FIG. 11. There it is apparent that the surface normal and hence the plane of the abutment face 410 is inclined or slanted with regard to the long axis D of the injection device 1 and of the body 401.

Figure 12:
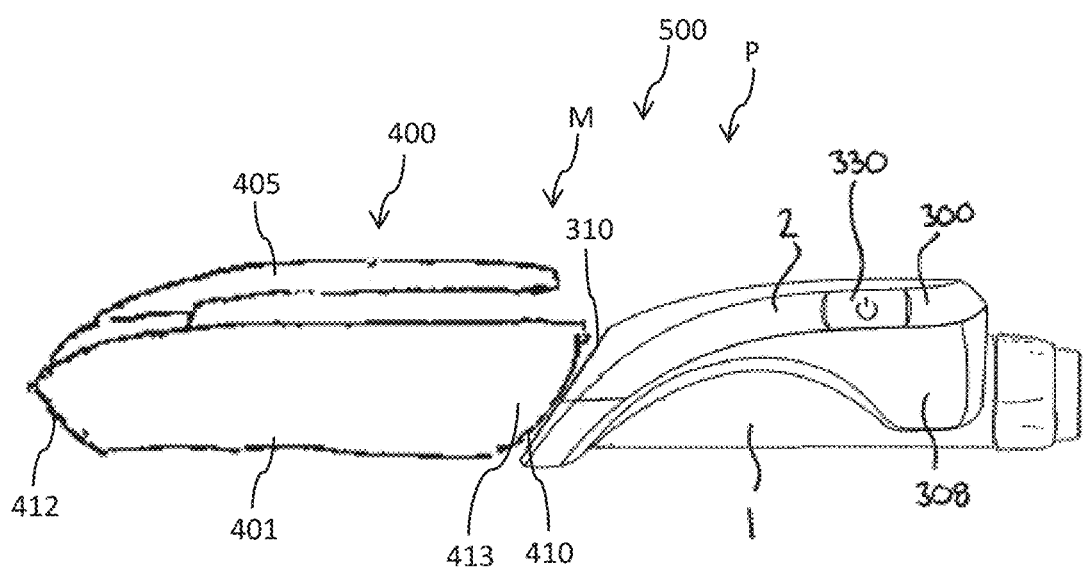
FIG. 12 shows a kit comprised of the injection device, the mounting aid and the supplementary device attached to the injection device.
Figure 13:
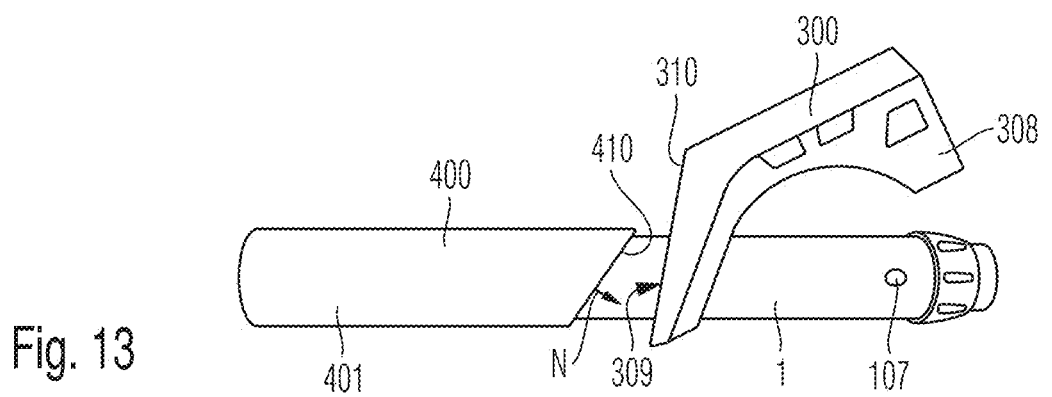
FIG. 13 shows the kit during or prior to the assembly of the supplementary device to the injection device to which the mounting aid is preassembled.
Figure 14:
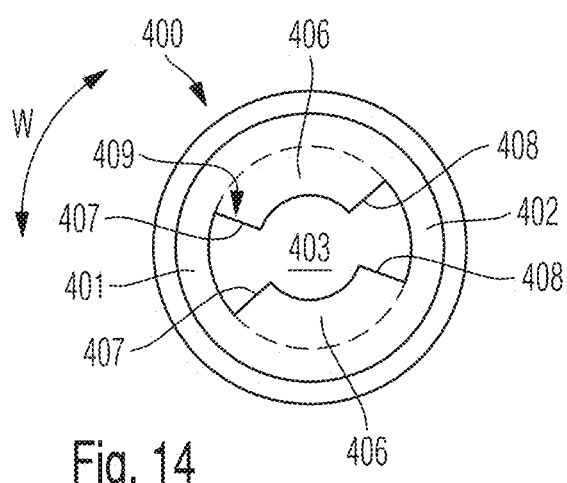
FIG. 14 is a cross-section through the mounting aid.

This inclination of the somewhat planar abutment face 410 represents a symmetry-breaking feature that corresponds to a complementary-shaped symmetry-breaking feature of the supplementary device 2. As shown in FIGS. 5 and 12 the distally facing front face 310 of the supplementary device 2 is also somewhat inclined with regard to the longitudinal axis B of the supplementary device 2. The inclination of the supplementary device's abutment face 310 and the inclination of the abutment face 410 of the mounting aid 400 mutually correspond so as to completely align when the supplementary device is correctly mounted and attached to the injection device. The inclined abutment face 410 serves as a tactile and visually detectable mounting support for correctly assembling the supplementary device 2 onto the outside surface 106 of the injection device 1.

The proximal end 413 of the mounting aid 400 may be located proximally from the shoulder 103 of the housing 10 of the injection device 1. It is hence conceivable that the housing of the device 10 is shoulder-free and the proximal end face 310 of the mounting aid 400 forms a rim like shoulder providing a proximally facing but distally located abutment face for the correct and specific assembly and attachment of the supplementary device 2 to the injection device 1. Consequently the axial elongation of the mounting aid 400 may exceed the axial elongation of the housing's front section 101 or of the cartridge holder 450 forming such the front section 101.

A kit 500 comprised of the injection device 1, the supplementary device 2 and the mounting aid 400 assembled to the injection device is illustrated in FIG. 12. The mounting aid 400 is assembled and fixed to the injection device 1 in a specific position M relative to the injection device 1 thereby defining a specific position P for assembling the supplementary device 2 to the injection device 1. The mutually corresponding abutment faces 310 and 410 mutually abut or engage along the entire circumference of the side wall 452 and the collar 301.

Figure 15:
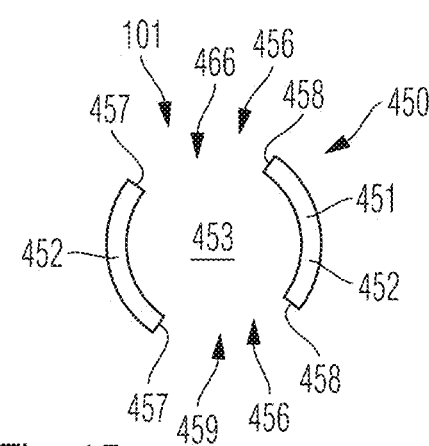
FIG. 15 is a cross-section through a distal section of the injection device.

As it is shown in more detail in FIGS. 14, 16-18 the mounting aid 400 comprises two radially inwardly extending engaging members 406, 416 by way of which the mounting aid 400 is fixable and attachable to the housing 10 of the injection device 1. In the illustrated embodiment the engaging members 406, 416 extend radially inwardly from the sidewall 402 of the body 401. By means of the engaging member 406 the mounting aid 400 is axially as well as tangentially fixable to the distal section 101 of the injection device 1. As it is shown in more detail in FIG. 15 the distal section 101, typically configured as a cartridge holder 450, comprises a tubular-shaped body 451 with a sidewall 452. At least in the axial section that is shown in FIG. 15 the sidewall 452 comprises two geometrically oppositely located engaging members 456 that are configured as longitudinal slits 466. Each one of the engaging members 456 comprises two tangential side edges 457, 458 as well as a distal edge 472 forming a distal axial stop 471 and a proximal edge 462 forming a proximal axial stop 461.

The lateral side edges 457, 458 form a tangential stop 459 for the engaging members 406, 416 of the mounting aid 400. When engaged and fastened to the injection device 1 a side edge 408 of the engaging member 406 gets in tangential or circumferential abutment with the side edge 458 thereby forming a tangential stop 409. Correspondingly, also the oppositely located side edge 407 engages in tangential direction (w) with an oppositely located side edge 457 of the body 451. In this way a tangential or circumferential stop 459 is provided on the body 451 by way of which the mounting aid 400 is rotationally lockable or locked to the housing 10 of the injection device 1.

Figure 16:
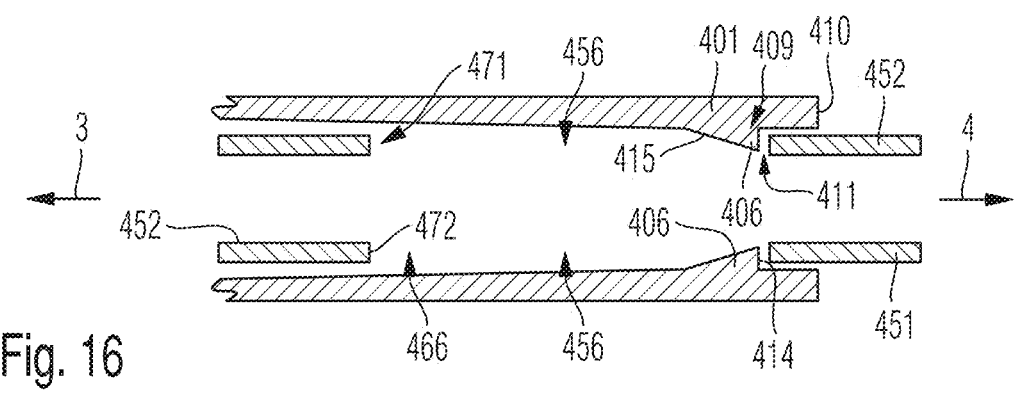
FIG. 16 is a longitudinal cross-section through the distal section of the injection device with the mounting aid attached thereto according to a first embodiment.

With regard to the longitudinal axis the sketch of FIG. 16 shows that the radially inwardly extending engaging members 406 of the mounting aid 400 comprise a radially inwardly extending proximal edge 414 that is configured to axially abut with the distally facing edge 462 of the engaging member 456 of the cartridge holder 450 thereby forming an axial stop 411. The mutual abutment between the engaging members 406 with the recessed engaging member 456 therefore blocks a proximally directed displacement of the mounting aid 400 relative to the injection device 1. The axial positions of the engaging members 406, 456 therefore define the axial component of the specific position of the supplementary device 2 with regard to the injection device 1. A distally directed displacement of the mounting aid 400 with regard to the injection device 1 could be also implemented by a frictional engagement between the bodies 451, 401, which is not necessarily illustrated here.

Figure 17:
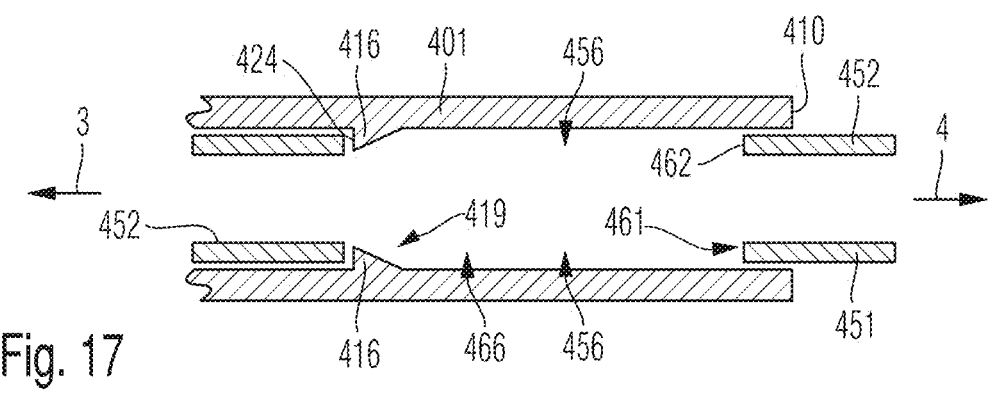
FIG. 17 shows an alternative embodiment of a configuration according to FIG. 16.

In another embodiment partially illustrated in FIG. 17 the mounting aid 400 could be fastened to the injection device 1 with regard to the proximal direction 4 by means of a frictional engagement, which is not further illustrated. However, in distal direction 3, hence for blocking a distally directed displacement of the mounting aid 400 with regard to the injection device 1 there are provided engaging members 416 on the inside of the sidewall 402 of the mounting aid 400. Likewise the engaging members 406 as described above in connection with FIG. 16 the engaging members 416 according to FIG. 17 comprise a rather steep and radially extending distal edge 424 that acts as an axial stop 421. Lateral side edges of the engaging members 416 also form a tangential stop 419 to engage with the side edges 457, 458 in the side wall 452 of the body 451.

As illustrated in FIG. 17 the distal edges 424 of the engaging members 416 get in axial abutment with the proximally facing edge 472 of the slit 466 in the sidewall 452 of the cartridge holder 450. Due to the mutual abutment of the distal edges 424 with the proximal edges 472 the mounting aid 400 cannot be displaced any further in distal direction 3 relative to the injection device 1.

Figure 18:
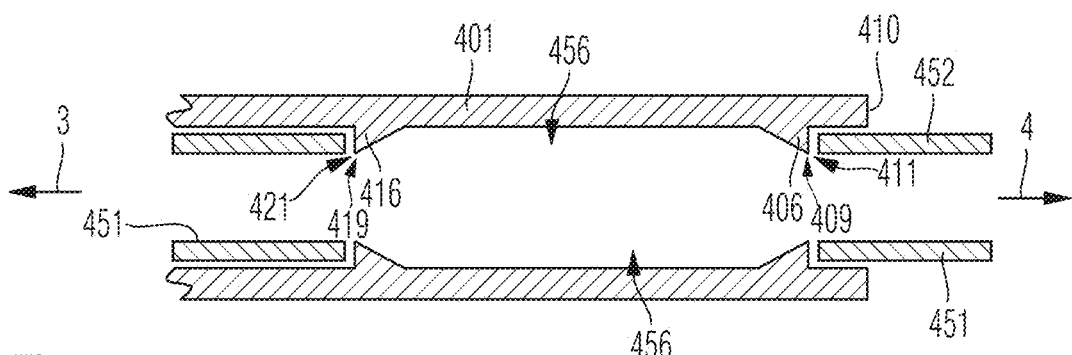
FIG. 18 shows a third embodiment of the mutual fixing of the mounting aid and the injection device in accordance to the illustration of FIG. 16.

In the further embodiment as shown in FIG. 18 the mounting aid 400 comprises two different types of radially extending engaging members 406, 416. Here and as described above in connection with FIGS. 16 and 17 the engaging members 406 provide a proximally facing stop 411 preventing any further displacement of the mounting aid in proximal direction relative to the injection device 1 whereas the engaging members 416 provide a distally facing stop 421 preventing a further distally directed displacement of the mounting aid 400 relative to the injection device 1. Alternatively it is conceivable, that the bidirectional axial as well as tangential mutual fixing between the mounting aid 400 and the injection device 1 is provided by only one pair of engaging members 406, 456 on the inside of the body 401 and on the outside of the cartridge holder 450. It is generally sufficient when the body 401 comprises only one radially inwardly extending protrusion 406 that matches in shape and geometry with a correspondingly-shaped recess on the outside surface 106 of the injection device 1.

The embodiment according to FIG. 16, wherein the radially inwardly extending engaging member 406 comprises a beveled portion 415, a disconnection of the mounting aid 400 from the injection device is rather simple and straight forward. For disassembling the mounting aid 400 from the injection device 1 the mounting aid 400 will have to be pushed or drawn in distal direction 3 relative to the injection device 1. The beveled portion 415 engaging with the proximal edge 472 of the slit 466 may lead to a temporary radial widening of the body 401 until the mounting aid 400 has been completely disassembled from the injection device 1. For inserting the injection device 1 into the receptacle 403 of the mounting aid 400 a corresponding radial widening of the body 401 may be induced by means of a radially widening shoulder portion near a distal end of the distal housing section 101 or near a distal end of the cartridge holder 450 (not illustrated).

In the embodiments as shown in FIGS. 14-18 the mutually corresponding engaging members 406, 416, 456 of the mounting aid 400 and of the injection device 1 enable two geometrically opposite mounting configurations for the mounting aid 400 to the injection device 1. The two different configurations differ by a rotation of the mounting aid 400 with regard to the longitudinal axis by 180°. However, for the supplementary device 2 to operate correctly it is required that the supplementary device 2 actually covers the display 13 of the proximal section 102 of the injection device 1. So in order to mount the mounting aid 400 correctly to the injection device 1 there is provided at least one label 430, 433, 444 on the outer surface of the body 401 of the mounting aid 400. The outside surface 106 is provided with a label 425 or indicator.

Figure 19:
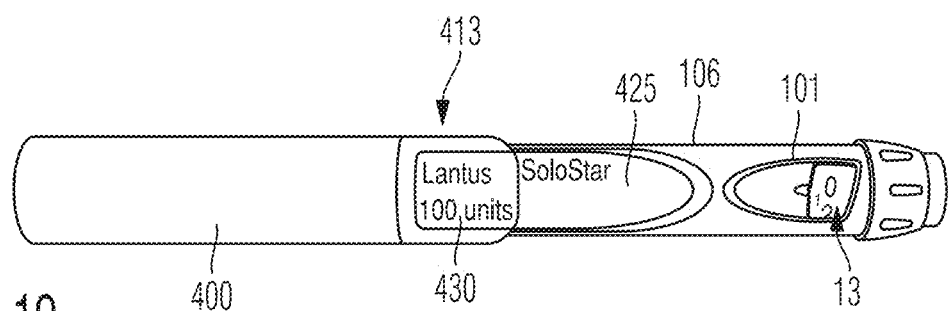
FIG. 19 is a top view onto the injection device with the mounting aid attached thereto, wherein a portion of the mounting aid covers a portion of a label on the outer circumference of the injection device and wherein the covered portion of said label is provided on the outer circumference of the mounting aid.

As shown in FIG. 19 the mounting aid 400 is actually covering a distal section of the label 425. In order to indicate or to visualize an unambiguous and correct attachment of the mounting aid 400 to the injection device the proximal end 413 of the mounting aid is provided with a label 430 that is equivalent or identical to that portion of the label 425 actually being covered by the mounting aid 400. So the partially covered label 425 on the outside surface 106 of the injection device 1 is completed by the label 430 on the outside surface of the mounting aid 400.

Figure 20:
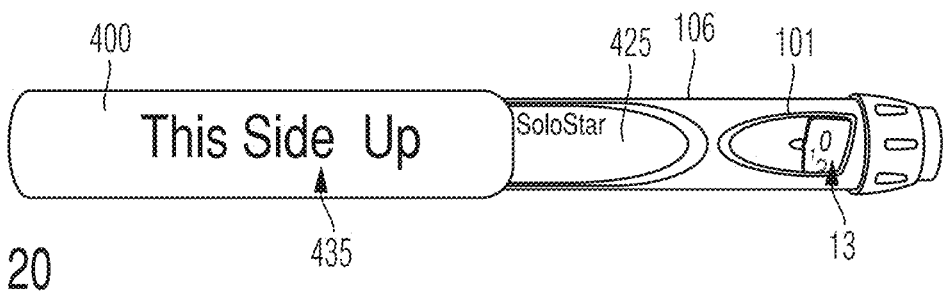
FIG. 20 is an alternative embodiment of the mounting aid with a different kind of label on its outside surface.
Figure 21:
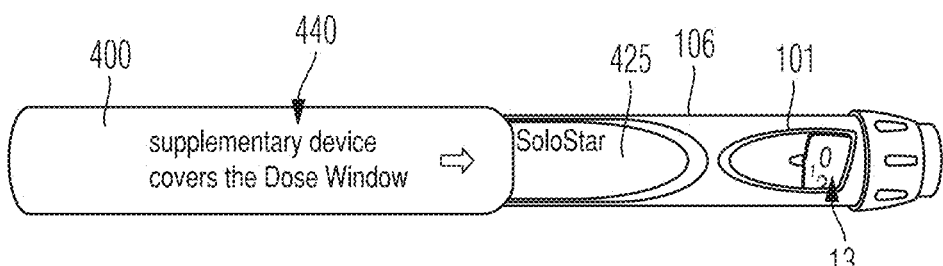
FIG. 21 is another alternative embodiment of the outside label of the mounting aid and FIG. 22 shows another embodiment of the mounting aid with a recessed portion at a proximal end to visualize a label on the outside surface of the injection device located underneath.
Figure 22:
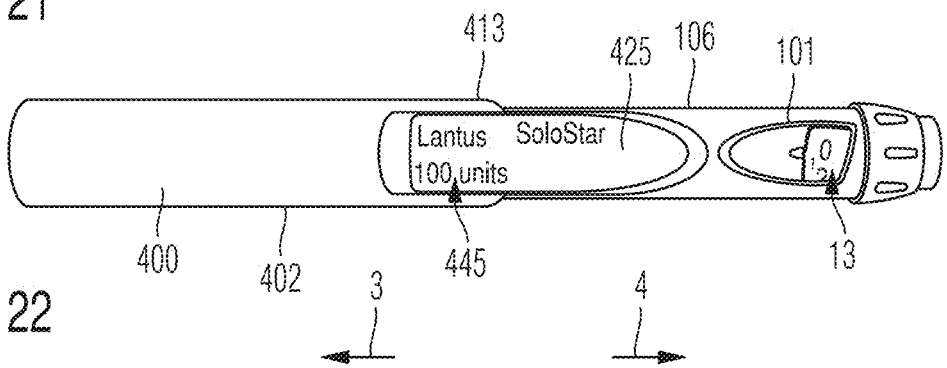

In FIG. 20 a different configuration of a label 435 on the outside surface of a mounting aid 400 is shown. This label 435 as well as the further label 440 as shown in FIG. 21, indicate that sidewall section of the injection device 1 that is equipped and provided with the display 13. In a further embodiment as shown in FIG. 22 the proximal end 413 of the body 401 of the mounting aid 400 is provided with a cutout or recess 445 extending from the proximal end 413 and hence from the proximally facing abutment face 410 in distal direction 3.

The size and shape of the recess 445 matches with that portion of the label 425 that would be otherwise covered by the mounting aid 400 in the embodiments as shown in FIG. 19-21. In the embodiment of FIG. 22 the recess 445 provides a complete and unobstructed view of the label 425 provided on the outside surface 106 of the injection device 1. Instead of the recess 445 it is also conceivable that the body 401 of the mounting aid 400 is just provided with a transparent portion filing the recess 445 so as to allow a complete visualization of the label 425 located underneath and which is at least partially covered by the sidewall 402 of the mounting aid 400.

The invention claimed is:

1. A mounting aid for attaching a supplementary device to an injection device the mounting aid comprising:
   a body extending in an axial direction, the body being configured to receive at least a portion of a housing of the injection device, wherein the housing of the injection device has an elongated shape extending in the axial direction,
      wherein the body comprises a first engaging member that extends radially to engage with a first housing engaging member of the housing when the body is in a specific position relative to the housing of the injection device, the first engaging member being configured to fix the body to the housing at least with regards to a circumferential direction and the axial direction, wherein the first engaging member further comprises a first axial stop facing in a distal direction and configured to axially abut with a first correspondingly shaped proximally facing axial stop of the first housing engaging member,
   wherein the body further comprises a second engaging member that is radially extending to engage with a second housing engaging member of the housing when the body is in the specific position relative to the housing, the second engaging member further comprises a second axial stop facing in a proximal direction and configured to axially abut with a second correspondingly shaped distally facing axial stop of the second housing engaging member, wherein the first engaging member and the second engaging member are offset from each other along the axial direction, and
   wherein the body comprises a side wall, the side wall comprising an abutment face located at a proximal end of the body and facing in a proximal direction, wherein the abutment face is defined on a plane that is inclined to the axial direction.

2. The mounting aid according to claim 1, wherein the abutment face of the mounting aid is planar and wherein an imaginary surface normal of the abutment face of the mounting aid extends non-parallel to the axial direction.

3. The mounting aid according to claim 1, wherein the body comprises a tubular shaped receptacle to enclose at least a distal section of the housing.

4. The mounting aid according to claim 3, wherein the body is cup shaped with a closed distal end section.

5. The mounting aid according to claim 3, wherein an inner cross section of a proximal end of the tubular shaped receptacle is larger than or equal to a cross section of a proximal section of the housing.

6. The mounting aid according to claim 1, wherein at least one of the first engaging member and the second engaging member of the mounting aid protrudes radially inwardly from the side wall of the body.

7. The mounting aid according to claim 1, wherein the first engaging member of the mounting aid comprises at least one tangential stop and the first housing engaging member of the housing comprises a correspondingly shaped tangential stop, wherein the at least one tangential stop of the mounting aid abuts in a tangential direction with the correspondingly shaped tangential stop of the first housing engaging member.

8. The mounting aid according to claim 7, wherein the at least one tangential stop of the mounting aid is formed by at least one tangential side edge of at least one of the first engaging member and the second engaging member of the mounting aid.

9. The mounting aid according to claim 1, wherein the body comprises a visual label on an outside surface or wherein the body comprises a distally extending recess at a proximal end of the side wall.

10. The mounting aid according to claim 1, wherein the abutment face represents a symmetry-breaking feature and is shaped and configured to align and to abut with a complementary-shaped corresponding abutment face of the supplementary device upon attaching the supplementary device to the injection device.

11. The mounting aid according to claim 1, wherein the first axial stop facing in the distal direction and the second axial stop facing in the proximal direction are configured to simultaneously engage with the first correspondingly shaped proximally facing axial stop of the first housing engaging member and the second correspondingly shaped distally facing axial stop of the second housing engaging member.

12. The mounting aid according to claim 1, wherein each of the first engaging member and the second engaging member comprise a pair of radially symmetric components.

13. The mounting aid according to claim 1, wherein the first engaging member is engageable with the first correspondingly shaped proximally facing axial stop of the first housing engaging member, which is provided at a distal edge of a longitudinal slit of the elongated shape and wherein the second engaging member is engageable with the second correspondingly shaped distally facing axial stop of the second housing engaging member provided at a proximal edge of the longitudinal slit of the elongated housing.

* * * * *